United States Patent [19]
Boudjema

[11] Patent Number: 5,662,661
[45] Date of Patent: Sep. 2, 1997

[54] INSTRUMENT FOR CUTTING CALIBRATED HAIR GRAFTS

[75] Inventor: Pascal Boudjema, Paris, France

[73] Assignee: Medicamat S.A., Malakoff, France

[21] Appl. No.: 425,381

[22] Filed: Apr. 20, 1995

[30] Foreign Application Priority Data

May 13, 1994 [FR] France .................................. 94 05884

[51] Int. Cl.$^6$ .................................................. A61B 17/50
[52] U.S. Cl. ............................ 606/132; 606/131; 606/167
[58] Field of Search ...................................... 606/131, 132, 606/133, 167, 172, 184, 185, 186, 187; 83/858, 699.11

[56] References Cited

U.S. PATENT DOCUMENTS 3,867,942  2/1975  Bellantoni et al. .

FOREIGN PATENT DOCUMENTS 1351653  12/1963  France .
3432897  8/1984  Germany .

Primary Examiner—Robert A. Hafer
Assistant Examiner—Benjamin K. Koo
Attorney, Agent, or Firm—Christie, Parker & Hale, LLP

[57] ABSTRACT

The invention relates to a device for surgical cutting of strips of scalp into multiple calibrated hair grafts, of identical small size. The device has a blade holder designed to allow vertical positioning of multiple parallel and equidistant blades, so that the cutting edges of said blades are aligned in one and the same horizontal plane, these blades then projecting from a support surface, and a plate of flexible material is intended to be placed flush with the cutting edges of the blades and is associated with an applicator associated with retention or abutment and, if appropriate, guide means making it possible to apply or press this plate onto the cutting edges of the blades, parallel to said support surface, while ensuring that this plate does not move beyond a limit position set at a distance from the support surface which is greater than the thickness of the strips for which the surgical cutting device is intended.

10 Claims, 5 Drawing Sheets

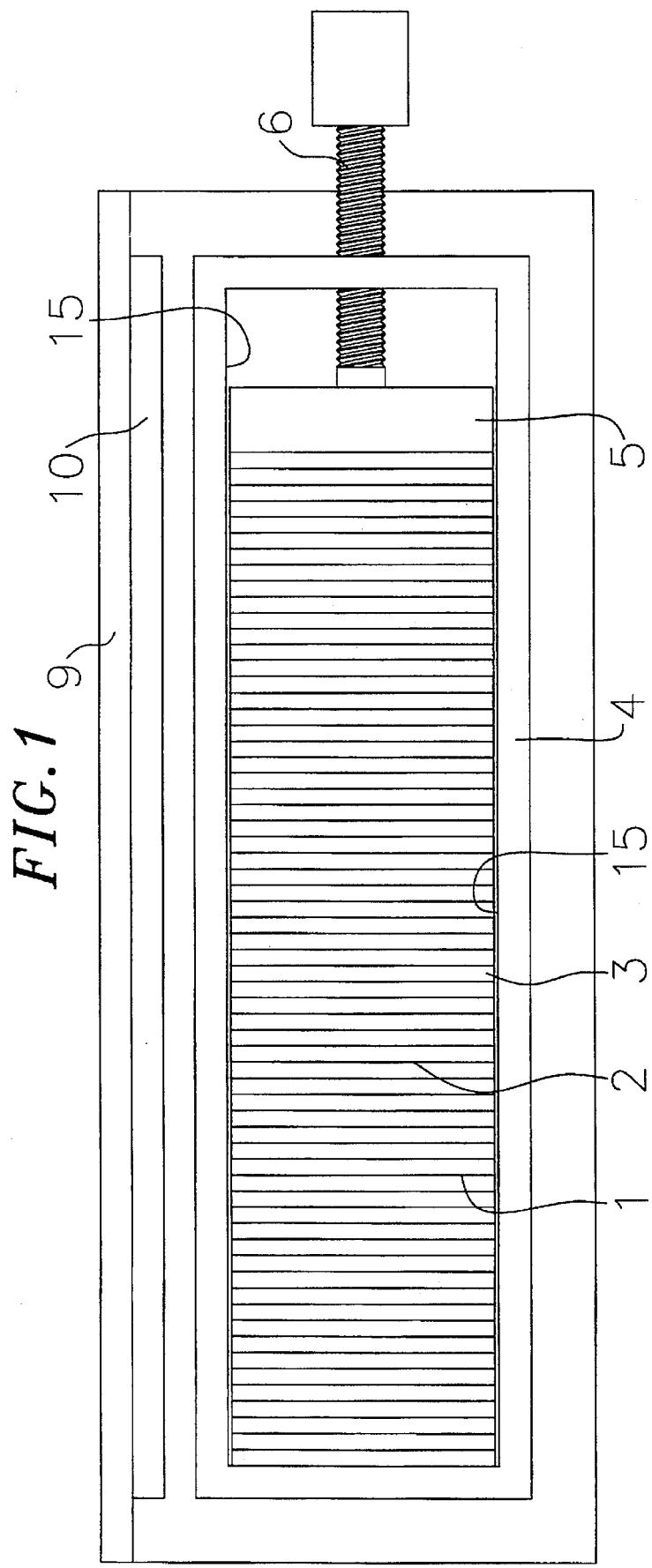

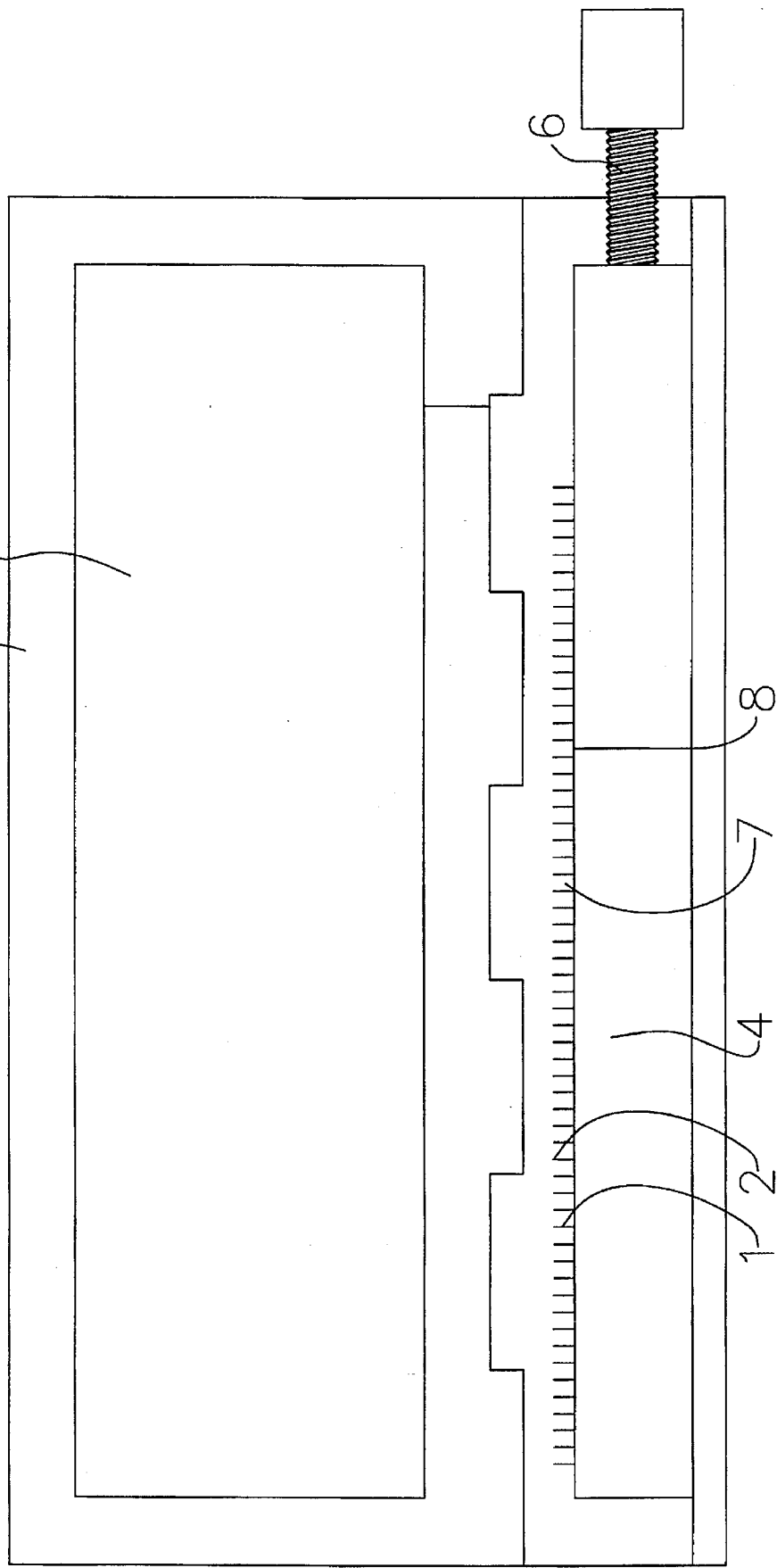

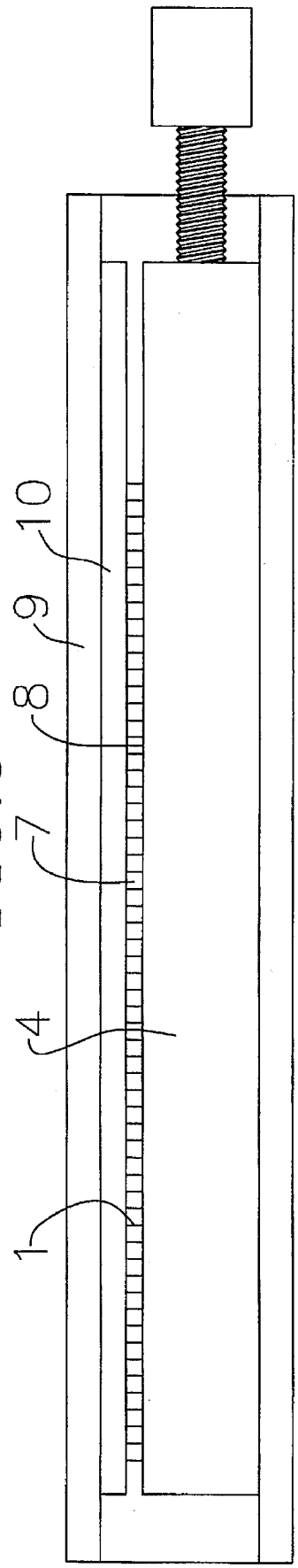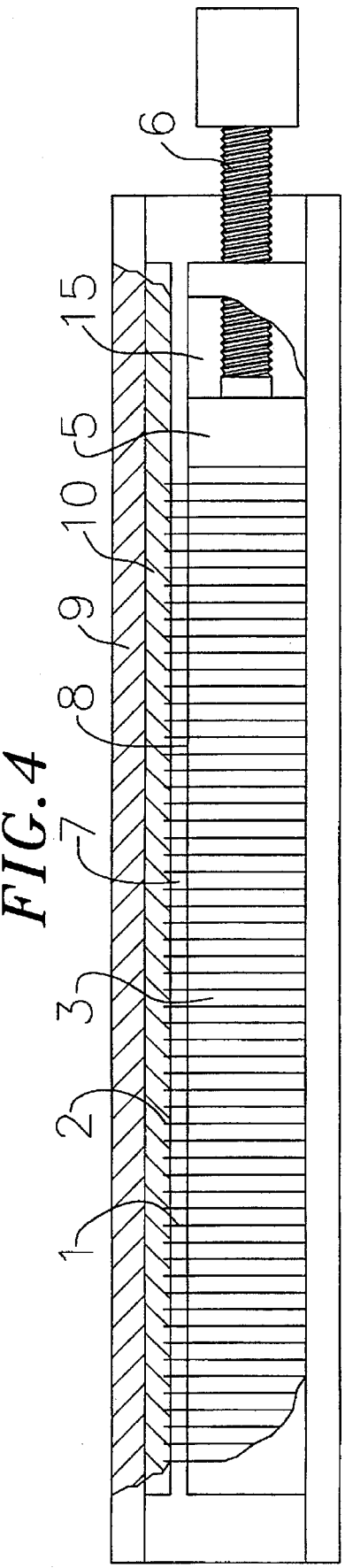

INSTRUMENT FOR CUTTING CALIBRATED HAIR GRAFTS

BACKGROUND

The present invention relates to a device for surgical cutting of strips of scalp into multiple identical, calibrated hair grafts of small size, comprising a cutting instrument having multiple equidistant parallel blades.

It finds a particularly important but not exclusive application in the field of the surgical treatment of alopecia by grafting the natural hair, and more particularly in the field of micrografting.

The surgical treatment of alopecia by hair transplantation, called the graft technique, consists in transplanting, in one and the same individual, some of the roots of his/her hairs located in the crown (still growing hair) onto the bald regions.

Micrografts of the scalp are, for example, obtained from a rectangular, elongated strip of skin measuring approximately 14 cm in length by 1.5 mm in width and 5 mm in depth, which contains hair roots and has previously been taken, from the occipital crown, using a knife consisting of a handle, at the end of which four to six cutting blades which are parallel, equidistant, and spaced apart by approximately 1.5 mm are mounted. This knife thus makes it possible to obtain 3 to 5 strips measuring approximately 1.5 mm in width and 14 cm in length (first operational step).

Each strip taken is then arranged flat, on a hard work surface and held by a clamp, then recut perpendicularly to its long axis, parallel to the axis of the roots, using a single-blade knife, into several hundreds of micrografts of quadrilateral shape, the size of which varies from 1 to 3 mm in width, and each of which contains one to four roots (second operational step).

The grafts thus obtained are then reimplanted one at a time into small reception orifices arranged in the bald regions (third operational step).

Unfortunately, since the micrografts obtained do not have the same dimension and are not calibrated and homogeneous, given that they are cut by sight and free hand, they do not fit perfectly into the reception orifices and, furthermore, manual cutting of the strips is time-consuming and tedious.

SUMMARY

The present invention aims to eliminate the drawbacks listed above by providing a device and a method which are better suited than those of the prior art to the practical requirements, in particular by making it possible to rapidly and simultaneously cut the strips of scalp into multiple, perfectly identical, calibrated and homogeneous micrografts, at low cost, simply and in a manner which is easy to employ, and to do this essentially without impairing their integrity and, consequently, their capacity for subsequently being reimplanted into the bald regions.

For this purpose, the invention essentially provides a device for surgical cutting of strips of scalp into multiple calibrated hair grafts, of identical small size, combining The device has a blade holder or casing designed to allow vertical positioning of multiple parallel and equidistant blades, so that the cutting edges of said blades are aligned in one and the same horizontal plane, these blades then projecting from a support surface.

Further a plate of flexible material is intended to be placed flush with the cutting edges of the blades and is associated with an applicator associated with retention or abutment and if appropriate, guide means making it possible to apply or press this plate onto the cutting edges of the blades, parallel to said support surface, while ensuring that this plate does not move beyond a limit position set by the retention or abutment at a distance from the support surface which is greater than the thickness of the strips for which the surgical cutting device is intended.

Under these conditions, it is possible to cut the strips, once they have been placed on the cutting edges of the blades, by applying and pressing the plate onto the strip, until the plate reaches the abovementioned limit position, the blades then biting into the flexible material of the plate. It is naturally envisageable to reverse the steps: positioning the strips on the plate and moving the blades towards them.

The blade holder is thus normally organized so that the blades can be tightened against one another or, in contrast, untightened, in particular according to the desired caliber of the micrografts.

These operations are advantageously carried out by means of spacers between which the preferably removable blades are interposed, the outward pointing sides of which spacers define the support surface from which the blades project. Advantageously, these spacers themselves cooperate with guide surfaces or elements allowing them relative displacements in a direction perpendicular to the planes of these spacers, for example the internal surfaces of a casing in which they are normally housed with the blades, when the spacers are in place. If appropriate, the latter guide surfaces or elements also contribute to holding the blades in place, the spacers then being capable of being withdrawn from the device, for example by retracting some of these guide elements.

Advantageously, and in particular when the spacers and the blades are guided between the opposite internal faces of a casing, the applicator is associated with the lid of the casing, and for example projects from the internal surface of the lid, in order for the plate of flexible material to be applied onto the cutting edges of the blades, when the edges of the lid which surround the applicator bear, in the closure position, on the corresponding rims of the casing. Thus, the edges of the lid contacting the rims of the casing comprises the abutment.

It is obvious that the plate of flexible material should also be removable, in order for it to be possible to fit its replacement during successive uses of the device.

Numerous advantages and features of the present invention will emerge during the following description, made with reference to the attached drawings which give one embodiment according to the invention by way of explanation but without implying any limitation.

BRIEF DESCRIPTION OF THE DRAWINGS

In these drawings:

FIG. 1 is a top plan view of the device according to one embodiment of the invention, with the compression plate raised, FIG. 2 is a front view of the device in FIG. 1, FIG. 3 is a front view of the device, with the compression plate lowered, FIG. 4 is a section of FIG. 3.

DETAILED DESCRIPTION

Figures 5, 6:
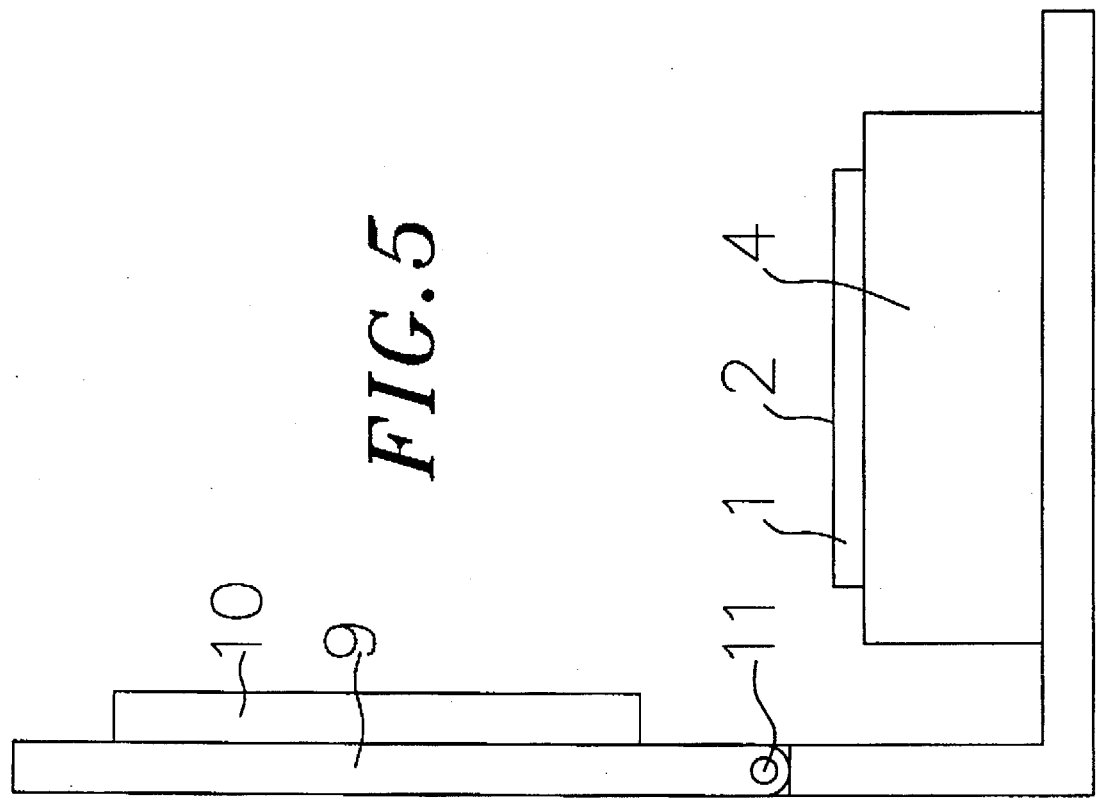
FIG. 5 is a side view of the device in FIG. 2.
FIG. 6 is a side view of the device in FIG. 3 and, FIG. 7 is a plan view of the device, indicating the position of two strips of scalp after cutting.
Figure 7:
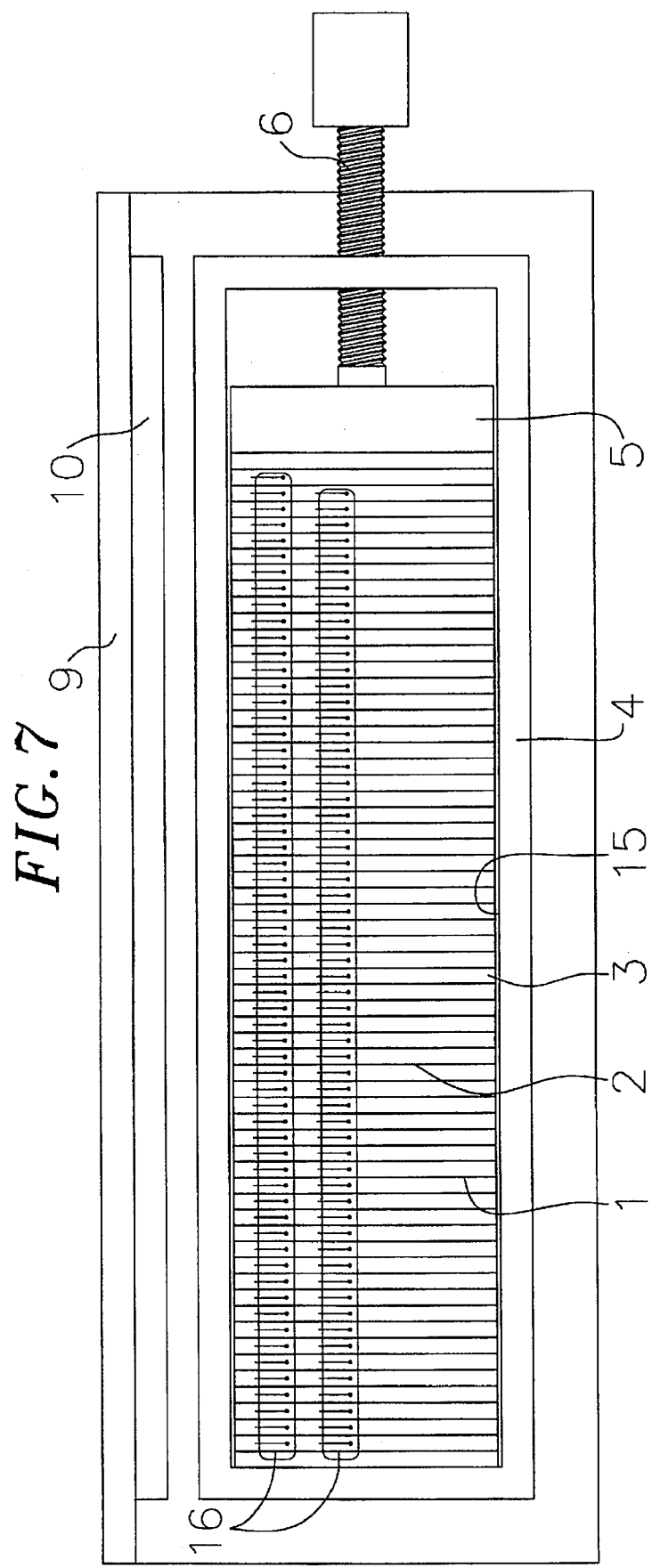

In FIGS. 1 to 6 it is seen that the surgical cutting instrument according to the invention consists of multiple cutting blades (1), which are of rectangular shape, aligned vertically, of the razor blade type, have a thickness of 0.1 mm, are mutually parallel and have straight cutting edges (2) measuring approximately 44 mm in length and arranged in one and the same horizontal plane. Said blades are equidistant, and separated from one another by intermediate plates (3) acting as spacers which also have a rectangular shape, are equal in length to the blades and have a determined thickness, for example 1.4 mm. The blades and intermediate plates are arranged inside an elongated casing or blade holder (4) and are held firmly tightened together by a block (5), made mobile by a threaded tightening rod (6), acting as a transverse vise. Guide surfaces, preferably the internal surfaces (15) of the casing (4), control the position of the spacers, and in a preferred embodiment, the guide surfaces preferably control the position of the blades. The guide surfaces allow the blades and spacers to move perpendicular to their respective planes, so that the transverse vise can compress them together to secure them in the casing.

The blades (1) have a height which is a few millimeters greater than that of the intermediate plates (3), the upper sides of which then define the support surface (8) (FIG. 2) so that a free space (7) can be arranged between said blades.

A rigid movable plate or applicator (9), acting as a press and having a rectangular shape makes it possible, by being folded down onto the casing (4) using a hinge (11) (FIG. 5), to compress an intermediate plate (10), of the pad type made of flexible plastic such as silicone, against the cutting edge (2) of the cutting blades (1).

As regards the cutting instrument according to the invention, the length of the casing (4) may be close to 21 cm so that it may contain more than a hundred cutting blades (1) spaced apart from one another by one hundred or more intermediate plates (3) having a thickness of 1 to 1.5 mm.

The intermediate plates (3) may be made of stainless steel.

The rigid plate (9) may be made of stainless steel.

In regarding to the rigid plate (9) supporting the flexible intermediate plate (10), although it has been represented such that it can be moved about a hinge (11) and folded down manually onto the casing (4), it is also possible to design it separated from the device proper then positioned by means of the flexible intermediate plate (10) against the cutting edges (2) of the blades, by vertical screwing of bolts.

The device according to the invention operates as follows:

The strips of scalp (16), previously taken from the crown, each measuring approximately 140 mm in length, 5 mm in width and 1.4 mm in thickness, are carefully deposited flat, over their entire length, on the cutting edge (2) of the cutting blades (1), of which there are one hundred. The orientation of the strips is such that the axis of the roots is parallel to the cutting blades (1).

Compressing the intermediate plate (10) of flexible material against the strips, by moving the rigid plate (9), allows instantaneous and simultaneous cutting of the strips into several hundred grafts located between the blades, in the free spaces (7). After the flexible intermediate plate (10) has been raised, untightening the threaded rod (6) acting as a transverse vise makes it possible to unwedge the grafts which are then recovered in order to be reimplanted.

I claim:

1. A device for surgical cutting of strips of scalp having thicknesses into multiple calibrated hair grafts, of identical small size comprising:

a blade holder;

a plurality of vertically positioned blades projecting from a support surface, lying in parallel planes, and spaced at equal distances from each other, and the blades being disposed in the blade holder;

a plurality of cutting edges on the blades, the edges being aligned in a horizontal plane relative to the vertically positioned blades;

an intermediate plate of flexible material which is positioned to be flush with the cutting edges of the blades;

an applicator connected to the intermediate plate for pressing the intermediate plate onto the cutting edges of the blades when the intermediate plate is parallel to the support surface; and means for preventing the intermediate plate from moving beyond a limit position which is at a distance from the support surface that is greater than the thicknesses.

2. The device according to claim 1 further comprising a plurality of spacer plates disposed in the blade holder and placed in between the blades, and the support surface is defined by outward pointing sides of the spacer plates.

3. The device according to claim 2 comprising guide means and wherein the spacer plates are disposed along parallel planes which are parallel to the blade planes, and the spacer plates are adapted to achieve relative displacements, along the guide means, in a direction perpendicular to the planes of the spacer plates.

4. The device according to claim 1 wherein the applicator projects from an internal surface of a lid of the blade holder.

5. The device according to claim 1 wherein the plate of flexible material is removable.

6. The device according to claim 1 wherein the applicator is connected to a lid of the blade holder.

7. The device according to claim 1 wherein the blades define free spaces therebetween for receiving pieces from a cut strip of scalp.

8. The device according to claim 1 wherein the means for preventing the plate from moving beyond a limit position comprises an abutment comprising edges of the applicator contacting rims of the blade holder.

9. A device for surgical gutting of strips of scalp having thicknesses into multiple calibrated hair grafts, of identical small size comprising:

a blade holder;

a plurality of vertically positioned blades projecting from a support surface, lying in parallel planes, and spaced at equal distances from each other, and the blades being disposed in the blade holder;

a plurality of cutting edges on the blades, the edges being aligned in a horizontal plane relative to the vertically positioned blades;

a plate of flexible material which is positioned to be flush with the cutting edges of the blades;

an applicator connected to the plate for pressing the plate onto the cutting edges of the blades when the plate is parallel to the support surface;

means for preventing the plate from moving beyond a limit position which is at a distance from the support surface that is greater than the thicknesses;

means for guiding the blades, the guide means comprising internal surfaces of the blade holder; and a plurality of spacer plates disposed in the blade holder and placed in between the blades, the support surface being defined by outward pointing sides of the spacer plates, the spacer plates being disposed along parallel planes which are parallel to the blade planes and adapted to achieve relative displacements, along the guide means, in a direction perpendicular to the planes of the spacer plates.

10. A device for surgical cutting of strips of scalp having thicknesses into multiple calibrated hair grafts, of identical small size comprising:

a blade holder having opposing internal faces;

a plurality of vertically positioned blades projecting from a support surface, lying in parallel planes, and spaced at equal distances from each other, the blades being disposed in the blade holder and guided between the opposing internal faces;

a plurality of cutting edges on the blades, the edges being aligned in a horizontal plane relative to the vertically positioned blades;

a plate of flexible material which is positioned to be flush with the cutting edges of the blades;

an applicator connected to the plate for pressing the plate onto the cutting edges of the blades when the plate is parallel to the support surface, the applicator comprising a lid of the blade holder;

a plurality of spacer plates disposed in the blade holder and placed in between the blades, the spacer plates being guided between the opposing internal faces, the support surface being defined by outward pointing sides of the spacer plates; and means for preventing the plate from moving beyond a limit position which is at a distance from the support surface that is greater than the thicknesses.

* * * * *

UNITED STATES PATENT AND TRADEMARK OFFICE
CERTIFICATE OF CORRECTION

PATENT NO. : 5,662,661
DATED : September 2, 1997
INVENTOR(S) : Pascal Boudjema

It is certified that error appears in the above-indentified patent and that said Letters Patent is hereby corrected as shown below:

<u>TITLE PAGE</u>
Item [56] References Cited, insert the following references:
    U.S. PATENT DOCUMENTS
        3,613,242   12/1966   Hill et al...........606/132
        4,137,807    2/1979   Schaumberg...... 83/858
        4,173,826   11/1979   Leopoldi et al... 30/124
        4,346,634    8/1982   Jones................ 83/858
        5,245,902    9/1993   Pereira............. 83/858

FOREIGN PATENT DOCUMENTS
    1,124,956   11/1984   Sudan..............606/132

Abstract, line 7, replace "surface, and a plate" with -- surface. A plate --.
Column 3, line 41, change "regarding" to -- regard --.

Signed and Sealed this

Fourth Day of August, 1998

Attest:

BRUCE LEHMAN

*Attesting Officer*    *Commissioner of Patents and Trademarks*